(12) United States Patent
Singh (10) Patent No.: US 10,442,449 B2
(45) Date of Patent: Oct. 15, 2019

(54) VEHICLE MOUNTED MONITORING SYSTEM

(71) Applicant: Rail Vision Europe Ltd., Loughborough (GB)

(72) Inventor: Sameer Singh, Loughborough (GB)

(73) Assignee: Rail Vision Europe Ltd., Loughborough (GB)

(*) Notice: Subject to any disclaimer, the term of this patent is extended or adjusted under 35 U.S.C. 154(b) by 185 days.

(21) Appl. No.: 15/623,156

(22) Filed: Jun. 14, 2017

(65) Prior Publication Data
US 2018/0208221 A1 Jul. 26, 2018

(30) Foreign Application Priority Data
Jan. 26, 2017 (EP) .................................. 17153355

(51) Int. Cl.
| | |
|---|---|
| *B61K 9/00* | (2006.01) |
| *G01J 5/02* | (2006.01) |
| *G01N 25/72* | (2006.01) |
| *G07C 5/00* | (2006.01) |
| *G07C 5/08* | (2006.01) |
| *B61K 9/06* | (2006.01) |
| *B61L 15/00* | (2006.01) |
| *G01J 5/00* | (2006.01) |
| *G01N 29/14* | (2006.01) |
| *G01N 29/04* | (2006.01) |

(52) U.S. Cl.
CPC .................. *B61K 9/00* (2013.01); *B61K 9/06* (2013.01); *B61L 15/0081* (2013.01); *G01J 5/025* (2013.01); *G01N 25/72* (2013.01); *G07C 5/008* (2013.01); *G07C 5/0858* (2013.01); *G01J 2005/0077* (2013.01); *G01N 29/04* (2013.01); *G01N 29/14* (2013.01); *G01N 2291/2696* (2013.01)

(58) Field of Classification Search
USPC ........................................... 374/124
See application file for complete search history.

(56) References Cited

U.S. PATENT DOCUMENTS

| | | | | |
|---|---|---|---|---|
| 5,292,090 A | * | 3/1994 | Wetzel ..................... | B61K 9/04 105/451 |
| 2011/0282540 A1 | | 11/2011 | Armitage et al. | |
| 2013/0094535 A1 | * | 4/2013 | Agostini .................. | B61K 9/06 374/2 |
| 2014/0169398 A1 | * | 6/2014 | Arndt ...................... | G01K 1/026 374/1 |
| 2014/0321501 A1 | * | 10/2014 | Bartonek .............. | G01J 5/0809 374/121 |

(Continued)

FOREIGN PATENT DOCUMENTS

| | | |
|---|---|---|
| EP | 2650191 A1 | 10/2013 |
| WO | 2015081278 A1 | 6/2015 |
| WO | 2015100425 A1 | 7/2015 |

*Primary Examiner* — Mirellys Jagan
(74) *Attorney, Agent, or Firm* — Young Basile Hanlon & MacFarlane, P.C.

(57) ABSTRACT

An on-board monitoring system for bogies or railroad trucks monitors components over time. The system is modular comprising a first modular device for mounting on the vehicle next to a component to be monitored and passing data on to one or more further modular devices. Focussed data acquisition and ongoing monitoring of a component becomes possible. Data transmission and analysis is also considered.

18 Claims, 6 Drawing Sheets

(56) References Cited

U.S. PATENT DOCUMENTS

| | | | |
|---|---|---|---|
| 2015/0110151 A1* | 4/2015 | Sivathanu | G01J 5/0003 374/121 |
| 2016/0103083 A1* | 4/2016 | Bartonek | B61K 9/04 701/19 |
| 2018/0290670 A1* | 10/2018 | Nishimura | B61L 15/0081 |

* cited by examiner

VEHICLE MOUNTED MONITORING SYSTEM

CROSS REFERENCE TO RELATED APPLICATION

The present application claims priority to European Patent Application No. 17153355.7, filed Jan. 26, 2017, incorporated herein in its entirety.

TECHNICAL FIELD

The present invention relates to a vehicle mounted system and method for monitoring vehicle components during use. In particular, the invention relates to an on-board monitoring system for bogies or railroad trucks and to the monitoring of components over time.

BACKGROUND

Rolling stock bogies on passenger and freight trains experience a range of stresses which cause their components to fail over time. Failures can be age related, but can also occur for a number of different reasons including operational conditions, manufacturing faults, heavy vehicle load, abnormal rail-wheel interface, poor lubrication, improper mounting or handling and weather conditions.

As a result, bogie health cannot be predicted purely based on factors such as age, and it is therefore important that bogies are monitored at regular intervals to ensure that any components that have failed or are about to fail are detected and replaced or repaired as required. The consequences of failing to detect a failed or failing component can be catastrophic, so it is important that such components are identified as quickly and as reliable as possible. As a result, it is known to employ trackside monitoring of bogies during use rather than relying only on periodic inspections of the rolling stock.

Each component has a normal operational temperature, acoustic and vibration emission which varies within reasonable bounds in operation. For example, the usual operating temperature for a wheel bearing is around 20° C. above ambient, while 70° C. or more above ambient would indicate a failure.

Known trackside monitoring solutions include Hot Axle Box Detectors (HABD) and Hot Wheel Detectors (WWD), both of which are temperature measurement devices that can be installed on trackside. A train detection system triggers a number of infrared probes/sensors which can be installed on either or both sides of the track as a train approaches. As the bogie comes into view of the sensor, the temperature at various parts of the bogie can be detected by the infrared sensors. A number of bogie components including wheel bearings, axle, brakes, motor and gearbox emit abnormal heat patterns when under stress or about to fail. Accordingly, the temperature readings can indicate faulty or failing components in wheels and bearings as well as, to a limited extent, faults in brakes, axles and/or other components.

The ability to rely on abnormal heat signatures generated during operation provides a clear benefit over static inspection of bogies, but there remain a number of significant shortcomings or disadvantages with this type of trackside monitoring.

Firstly, weather conditions can greatly influence the operation of a trackside system. Infrared detector capability is dependent on the intensity or amount of the received radiation, which can be heavily influenced by external environmental conditions such as snow, wind or rain. Alternatively, the infrared detection device may become saturated when directly exposed to sunlight or an intense reflection off a shiny surface, causing the detector to report artificially high heat levels. Strong sunlight can also lead to a piezo-electric effect which cases pyroelectric devices to produce false heat signals and report high levels of voltage.

Secondly, the detector area of these trackside devices is typically very small, often only 1 pixel or 2×2 pixels in resolution. As a result, the trackside sensors only generate point based measurements, providing no indication of how the heat is distributed across the component. Perhaps more significantly, there is a risk that the component of interest will not be scanned by the trackside detector. Unless the relevant component surface (wheel, bearing axle, brakes, etc) falls precisely within the detector's field of view, accurate readings cannot be made. Numerous different designs of bogie exist, with the size of wheels and the appearance and/or location of components varying between the designs. This leads to inconsistencies in the locations of interest and also potentially the lines of sight from a trackside location, which must be clear in order for accurate measurements to be made. Accurate timing is also necessary to measure a surface that is passing in front of the sensor at a very high speed relative to the static detector.

The static nature of trackside inspection systems also makes it all but impossible of them to acquire or maintain any data relating to how a particular bogie or component is performing. They can reactively sense a fault, but do not possess historic data for each bogie which could be used to any analytical tools for a better understanding the reasons behind the fault. Indeed, no information would typically be provided about where on a train a fault occurred, simply that a fault was present somewhere.

Finally, trackside devices can be relatively expensive to manufacture and install, so there will often be gaps of 4-5 miles, or in some cases up to 25 miles, between installations. Temperature increases in a failed bearing can be very rapid, eg from around 70° C. above ambient to around 300° C. above ambient in less than a mile. It is therefore quite conceivable that a failure could occur between installations, and not be detected in time for appropriate action to be taken.

These various factors can all lead to unacceptably high instances of missed detections and/or false positives.

SUMMARY

It is an object of the present invention to provide a monitoring system that overcomes or substantially mitigates one or more of the above problems.

According to a first aspect of the invention there is provided a vehicle mountable modular monitoring system, for monitoring one or more components of a bogie or railroad truck, as described in appended claim 1. Further beneficial features are recited in the associated dependent claims.

The system comprises first and second modular devices mountable to the vehicle, with the first modular device being configured for mounting adjacent a component to be monitored, and spaced from the second modular device. For example, the first modular device may be mounted on a bogie/railroad truck, adjacent a wheel or bearing to be monitored, and the second modular device may be mounted elsewhere on the carriage/car. The first modular device comprises a power source, one or more sensors including a non-contact temperature sensor for monitoring the temperature of said component, and a first wireless transmitter for transmitting data wirelessly from the first modular device to the second modular device. The second modular device comprising a wireless receiver for receiving data transmitted by the first modular device.

The first modular device may serve as a sensing device, for monitoring one or more components, with the second modular device serving as a receiver for receiving data from the first modular device and performing analysis on the received data. Alternatively, or additionally, the system may further comprise a third modular device for performing said analysis, and the second device may serve as a data transmission or relay device to transfer data between the first and third modular devices. One or more second modular devices may be provided.

The non-contact temperature sensor of the first modular device may be a thermal imaging sensor such as a thermopile for generating thermal images of the component. The digital thermopile array may have a size of 8×8, 16×16, 32×32, 64×64 or 128×128 pixels. The sensor may comprise a lens whose field of view determines the region of interest for temperature measurement. The position of the sensor can be fixed for a continuously monitored bogie component, so that the imaged area is known and fixed in advance. This will generate continuous time lapsed temperature profile for the same region over time.

Although contact sensors will typically have a lower power consumption, one important benefit of a non-contact thermal imaging sensor as described is that a matrix of thermal values can be obtained as opposed to a single measurement generated by a contact sensor. The temperature gradient over a surface area can be measured to show how the heat spreads across a component. A cross-section surface area can be analysed for average temperature as well as a change in temperature horizontally, vertically or radially outwards from a centre point, or at the interface between component surfaces.

Statistical information on the surface spread of the temperature is of considerable importance for understanding its source, and how it is likely to affect surrounding components. It also becomes possible to store and/or review statistical data on a component and process this to help understand component manufacturing faults, condition and predicted time to failure.

Known trackside thermal sensors also only generate point based measurements which cannot provide a similar temperature gradient over a surface.

In addition to a temperature sensor, the first modular device may also comprise one or more acoustic or ultrasonic sensors, for example a microphone assembly, for monitoring of certain bogie components. Acoustic technology can detect a failed or defective bearing, or other components, before the component has actually failed and emits a noticeable heat signature. As a result of this, the maintenance can be carried out offline and in good time rather than stopping the train as a matter of emergency. Components such as wheel bearings produce sounds at characteristic frequencies that depend on the type and location of the defect, size of the wheel and bearing capacity, and speed of the train. Further irregularities such as flats in the wheels also generate noise at additional frequencies.

Trains operate in fairly noisy environments, so a range of noise sources (such as rubbing of rail and wheel, flange and rail squeal, loose equipment and cargo, car body movement, track circuits and joints, wind, and external factors) can make the separation of acoustic signatures of interest difficult.

Advanced microphones have a range of built-in components for amplifying the sound detected and improving its signal to noise ratio. Given that the placement of the microphone assembly is fairly close to the bogie components it aims to monitor, there is a much better chance of detecting high frequency audio data that represent component failure. The microphone sensor not only provides information on audio data but the direction from where it is originating which makes it easy to isolate the faulty component. Spectral analysis of audio data uses techniques such as independent components analysis can be thereafter used to separate the detected signal into its components, where the characteristics of each signal can be measured such as its frequency, amplitude, and so on. Further classification can help identify signal components that come from faulty components when they occur.

It is known to use track-side acoustic sensors to pick up unusual acoustic emissions from the bearings or other bogie components. For example, RailBam, is an acoustic monitoring system produced by TrackIQ and marketed by Siemens which can be placed trackside to detect early stage bearing damage. In addition to the usual difficulties of ensuring correct targeting and timing of the measurement of a passing surface, acoustic sensor performance decreases when a train is passing at high speed. For example, the Doppler effect can lead to obvious frequency shifts, frequency band expansion, and amplitude modulation for the recorded acoustic signal, which reduces the diagnostic performance. These problems are largely avoided if the acoustic sensor is mountable on the vehicle.

The first modular device may further comprise vibration sensors. Vibrations can be caused by a multitude of factors including bearing failures, loose components and a range of other defects. For example, axlebox bearing elements like rollers and inner ring raceways, as well as toothed wheels, all generate specific dynamic frequencies which can be detected and analysed with additional knowledge of geometry data and shaft speed. The bearings within the traction motor or gearbox can be monitored in a similar manner.

While vibration and acoustic based analysis is a known technology for assessing bogie components, the above-mentioned drawbacks mean that neither approach tends to give reliable information relating to likely component failure when used alone. However, these sensors can provide useful additional data when used in combination with a temperature sensor.

The power source of the first modular device may comprise a battery, preferably a motion charged battery. The second modular device may also be similarly powered.

The first modular device may generate alerts based on a comparison of sensor readings from the one or more sensors with one or more threshold values. The data transmitted from the first modular device may include said alerts and the associated raw sensor readings.

Where the second modular device functions as a data transmission or relay device, it may comprise a similar set of components to the first modular device, with the exception of the one or more sensors.

The modular monitoring system may further comprise a third modular device comprising a wireless receiver and the second modular device may comprise a wireless transmitter to relay the data received from a first modular device to the third modular device.

The third modular device may provide one or more of visual and audio output to a user based on the data, for example an alert relating to wear of failure of a component, received by the third modular device.

The third modular device may store received data for future statistical analysis. This can be of assistance in finding the root cause of a fault or failure of a component detected by the system. The third modular device may also comprise a transmitter to allow transmission of received data to a remote location. The transmitter may also allow confirmation that data, such as alarm data, from the first modular device has been received. Transmissions from the first modular device may then be stopped to conserve power.

The third modular device may comprise a base unit and a portable unit that can be disengaged from the base unit. The portable unit may comprise a transmitter and receiver to remain fully synchronised with the base unit.

The portable unit may comprise an RFID scanner and the first and/or the second modular devices may comprise an RFID tag for identification. This allows for unique identification of each first and/or the second modular devices, of which there will typically be many. The portable unit may also be capable of receiving and transmitting information to change their configuration settings if required.

A plurality of second modular devices may be provided to form a chain and relay data beyond the transmission range of the wireless transmitter of each second modular device.

The invention may thus provide a mesh network for data transmission between each first modular device responsible for monitoring components, using on-board routing via the second modular devices, and the third modular device which may be located in the locomotive. Relaying data in this way minimises the required range of each transmitter, and thus minimises power drain. Fail safe measures, such as GPRS transmitters, may also be provided to ensure reliable transfer of data in the case of a failure or break in the chain.

In one particular example a distributed sensor network consists of sensor modules, relay modules and a control module. The network may have a number of sensor modules (>0), associated relay module(s) and a control module. There may be multiple control modules.

The semi-adhoc network is formed whereby multiple sensors communicate through a nominated relay module. The relay module maintains two way communications between itself and the associated sensor(s). It also maintains two way communications with other neighbouring relay modules in the network. Additionally, the relay module at the periphery of the network communicates with the control unit. These inter communications may be in the form of wireless, wired, optical or any combination of these.

During normal operation a sensor module sends periodic messages to its associated relay module. All messages regardless of their content are time-stamped. Relay module acknowledges to the sensor module the receipt of the periodic message.

Under certain conditions additional messages are sent by the sensor module. These messages are received by the relay module and acknowledged. This message is then relayed to its neighbouring relay module(s). More than one relay module may receive the message and each one will acknowledge back. Message transmission then propagates through the network similarly. Thus, the message route from the original relay module will take multiple routes and finally reach the control unit. Many copies of the original message may be received by the control unit and it acknowledges the receipt of these messages. Control unit may also reply back with its message intended for the originating relay unit. In some cases, this may be considered as the acknowledge message. The control unit messages received by the relay module(s) are then propagated through the network as described above. Again multiple routes may be taken and many copies of the control units' message may be received by the originating relay module.

Data may also be requested from sensors by the associated relay module or the control unit and message propagation will be as detailed as above.

The network communications will primarily transmit and receive data and status information from the sensors. Additionally, the control unit may also, but not limited to, maintain communications for the purpose of:

Ad-hoc powering up/down of sensors and relay modules
Sensor/relay module network formation and re-organisation
Sensor Alarm operation The data transmitted from a first modular device and/or a second modular device may include location data of its mounting positon on the vehicle. This allows a visual map of the positions of first modular devices and/or a second modular devices on the rolling stock. As an alternative, the signal strength of the transmitted data at the third modular device may be used to determine the relative positions of first and/or second modular devices for mapping.

The sampling rate of the one or more sensors may be variable during use. For example, a lower general sampling rate may be used to minimise power drain, and may increase when sensor readings exceed a threshold indicating that a component may be failing.

Similarly, the transmission rate of the first and/or second modular devices may be variable during use to manage power drain and data traffic and ensure that the overall network can cope with the data it handles.

The first modular device and/or the second modular device may comprise one or more of an accelerometer and a gyroscopic sensor to detect movement of a vehicle and deactivate the one or more sensors or the transmitter when no movement is detected. The system can then start and stop automatically depending on whether the vehicle is in motion or not to avoid unnecessary power drain.

The first modular device may comprise a laser aligned with the field of the one or more sensors for aligning the one or more sensors with a component to be monitored when mounting the first device.

The first modular device may comprise a plurality of sensor types working in combination. For example, one or more acoustic and/or ultrasonic sensors and/or vibration sensors may be used in combination with the temperature sensor. The additional sensor may be focussed on the same component to provide additional information about its performance and possible degradation during use. The recognition of defective components and/or the generation an associated alarm may be based on analysis of the information provided collectively by said plurality of sensor types.

The invention also provides a method of monitoring a vehicle component over time, comprising the steps of arranging a sensor on a vehicle in a fixed relationship with a component to be monitored, taking periodic sensor readings relating to at least one of the temperature, vibration and noise emitted by the component during use, relaying data from said sensor readings to a location remote from the component and analysing said data to identify faults or predict failure of said component.

With trackside systems in existence today, predictive maintenance of vehicle borne components is not possible.

The method may be carried out using the system as previously described. In particular, the ability to collate data relating to a particular component and relate this to a known manufacturer or batch, as provided by aspects of the described system, can help to identify defects or trends with a certain batch or design of component and allow for predictive or preventative maintenance.

Statistical analytics tools can be used to predict problems before a component enters into a critical failure state or fails. Over a period of time, significant volumes of data on component condition can be collected and used for predictive maintenance. It is important to note that such historical data on component condition is not available with trackside monitoring equipment in use today.

Historical data can be charted and evaluated with statistical tools to differentiate between different types of problems, estimate time to failure and determine the root cause of the problems (manufacturing issues versus wear and tear). Tools that can perform data classification, clustering, forecasting and planning on such data may be provided. Classification tools may be used to classify component condition and determine severity of the problem. Multi-sensor data may be integrated for accurate decision making and novelty detector tools may be used to determine abnormal behaviour. Clustering tools may be used to cluster the data from multiple vehicles and sensors to determine similarities between feature values and to determine commonalities. For example, the clustering analysis may indicate that the same problem occurs with components that have similar loads, or similar other characteristics. Forecasting tools such as regression analysis may be used to determine performance decay over time, and time to failure for components. Such analysis can be multivariate taking into account various component and non-component features of operation. Finally, maintenance planning tools for corrective and predictive maintenance may be used by the end-user to manage the repair and replacement of components.

The proposed system provides a number of benefits in the inspection of components, particularly in detecting possible faults or failures through the analysis of heat signatures. Hot wheels, axles and brakes can lead to major accidents, often as a result of brake malfunction or bearing failure. Excessive heat is also transmitted by failing components such as motors or gearboxes. In each case, vibration and acoustic emissions are also affected whose patterns at the time of failure can be thought of as outliers to their normal operation patterns. However, when components fail, their temperature, acoustic and vibration emissions can rapidly increase beyond normal bounds within a fairly short period of time. A trackside inspection system cannot measure bogie vibration or acoustic information in real-time, or combine this information with thermal data for real-time decision making. This reduces the overall capability of a bogie inspection system as several defects which can be picked up through sensor combination are infeasible with a trackside monitoring system.

In order to reduce the chances of component failures between two successive trackside inspection systems, an on-board system that can detect problems in real-time is therefore highly preferable. On-board systems are also better suited to observing the operational behaviour of components over their life-span and can record a wealth of information on their behaviour during use. This can be used for understanding the root causes for their failure and predictive maintenance. Individual identification markers for each sensor or module, along with recorded data about their installation, enables identification of problems with particular design or batch of wheels/bearings, or resulting certain loads or types of use. For example, wheelsets are typically only replaced roughly every 1.2 million kilometers of operation, and the invention provides a cost-effective solution to monitor these components during their lifetime and to report on both critical as well as potential future-critical issues.

The entire system is designed for low power consumption, with an effective communication protocol for alarm transmission, and maximising benefits from continuous monitoring of components as opposed to interval based monitoring which is used by trackside inspection devices. The overall design allows for the configuration of various parameters. For example, the sensing rate, and sleep pattern for various components can be adjusted to reduce power requirements of the component and therefore the overall system.

Similarly, the thresholds for detecting alarms can be adjusted as required. The overall approach uses a range of analytic methods to determine abnormal thermal, acoustic and vibration patterns, and raises an alarm when a component is found to be defective. The alarm is transmitted to the train driver so that immediate action can be taken, and also transmitted to a remote operational command centre.

Physical connections between components are minimised, therefore simplifying installation. A modular approach also ensures that the system works without any intervention when carriages are interchanged between trains.

Wherever practicable, any of the essential or preferable features defined in relation to any one aspect of the invention may be applied to any further aspect. Accordingly, the invention may comprise various alternative configurations of the features defined above.

BRIEF DESCRIPTION OF THE DRAWINGS

Practicable embodiments of the invention are described in further detail below by way of example only with reference to the accompanying drawings, of which.

DETAILED DESCRIPTION OF THE EMBODIMENTS

Figure 1:
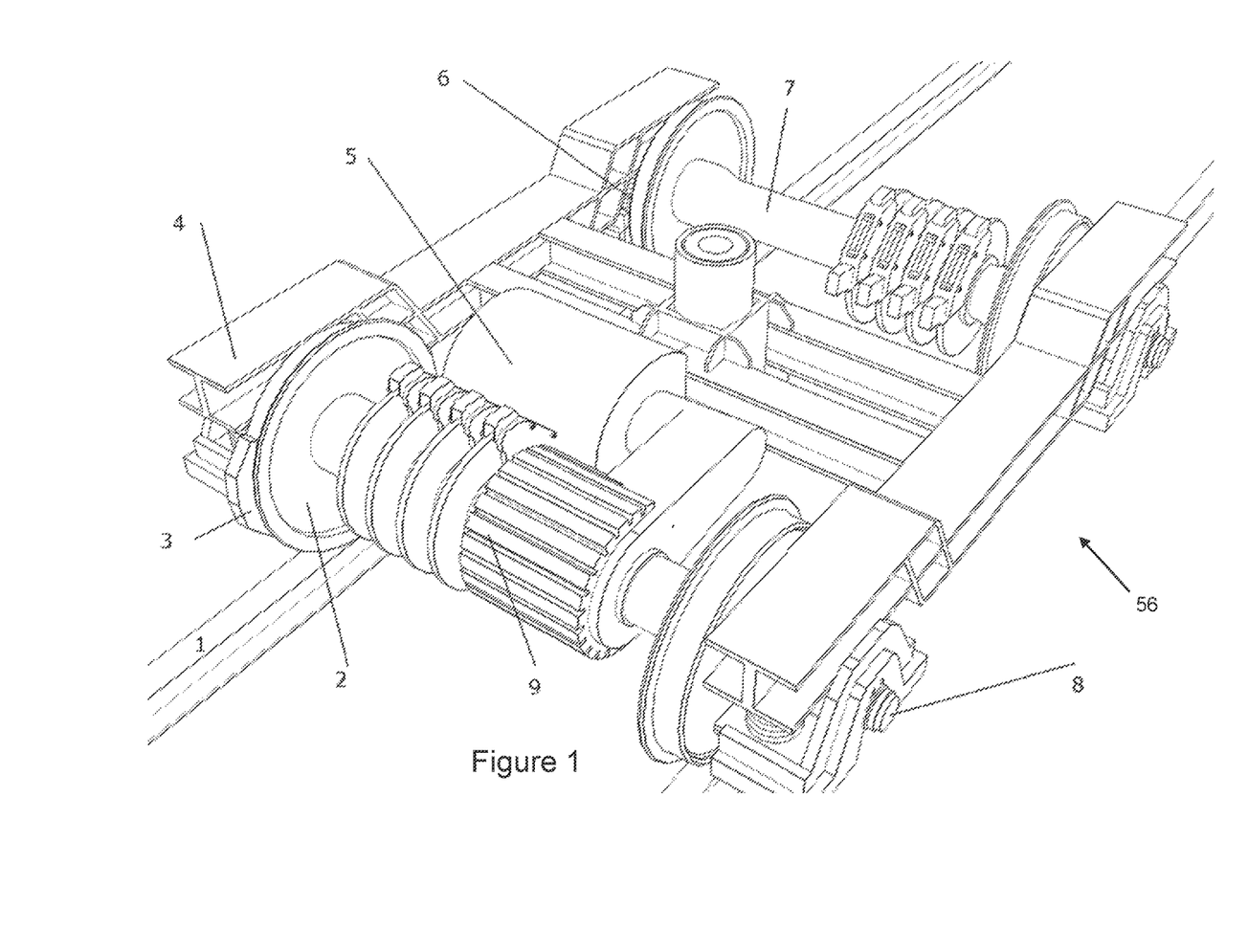
FIG. 1 shows a bogie/railroad truck.

FIG. 1 illustrates the main components of a bogie/railroad truck 56 which are of interest in the detection of failures. As set out above, the design of individual bogies can vary quite significantly, but FIG. 1 is included to provide an indication of the number of components which should be monitored and the potential difficulties in assessing these components from a remote, trackside, location.

The bogie 56 of FIG. 1 is shown with its wheels 2 running along rails 1. In very general terms, the bogie comprises front and rear pairs of wheels 2 each joined by axles 7 extending between side frame assemblies 4. One of the brakes 3 can be seen at the outer circumference of one wheel 2, and the location of the suspension 6, between the side frame 4 and the axle 7, is also indicated. Bearings 8 are provided in hubcap assemblies at the ends of each axle 7, while a gearbox 5 and motor 9 are shown towards the centre of one of the axles 7.

It should be clear from FIG. 1 that, only the bearing assemblies 8 will be clearly accessible/visible to a trackside detection device when the train is in operation. The remaining components will be at least partially obscured by the side frame assemblies 4 of the bogie and the carriage or container above. Centrally mounted components such as the gearbox 5 and motor 9 are particularly inaccessible, being additionally obscured by the wheels 2 of the bogie.

The invention addresses this problem by providing a monitoring system that can obtain sensor readings from a location on the bogie itself, in the most useful or appropriate position to monitor each component of interest. The system comprises three main modular devices, each of which will be described in turn.

Figure 2:
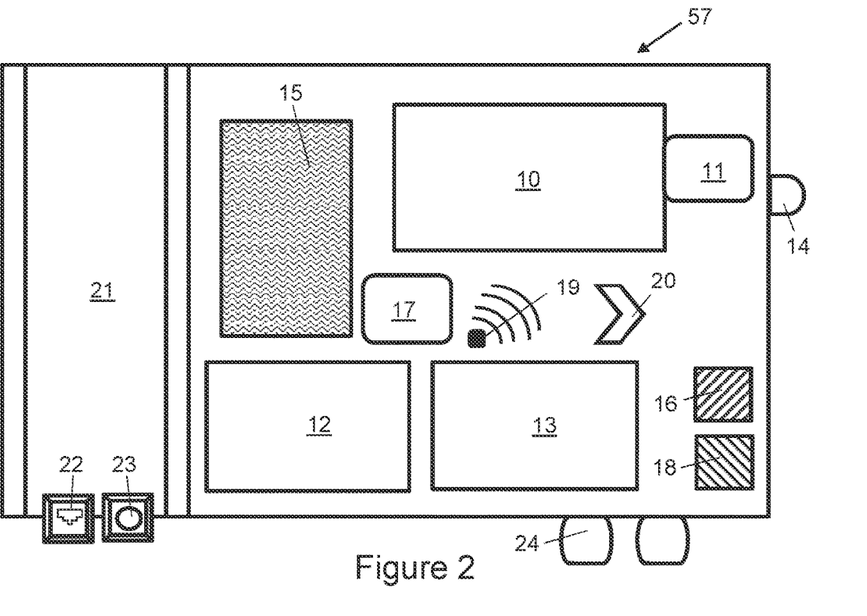
FIG. 2 shows a schematic view of a bogie sensor device unit (BSDU) according to the present invention.

The first modular device, called a "Bogie Sensor Device Unit" or BSDU for short, is shown schematically in FIG. 2. The BSDU 57 is a self-contained unit comprising a number of sensors for detecting faults or failures, along with a processor and transmitter and receivers for communication with other elements of the system.

A thermal sensor 10 is provided in the form of a digital thermopile array of size 8×8 or higher which is correctly calibrated to read the temperature of the surface in view, and ambient temperature. A thermal imaging lens 11 is also provided so that the thermal sensor 10 can be directed to a surface area of interest with a fixed field of view. The lens 11 also allows the field of view to be modified so that, for example, a single pixel in the thermal image output covers a fixed millimeter square area on the imaged surface. This provides improved freedom in the mounting position of the BSDU 57, as may be required to account for different configurations and component spacings on different bogies.

The analogue voltage data generated by the array of the thermal sensor 10 is converted into precise temperature readings in degrees centigrade which is recorded in real-time at a fixed pre-set interval.

An acoustic sensor 12 is also provided within the BSDU 57. The acoustic sensor 12 could be a microphone array or high frequency ultrasonic sensor measuring data at up to 100 KHz providing information at high resolution. Use of a microphone with directional input allows the acoustic sensor 12 to be directed to a particular target area of interest.

A vibration sensor 13 is also provided to measure the vibration experienced by the BSDU 57. The vibration sensor 13 will measure the entire audible frequency range of 20-20 KHz. The vibration observed will be a complex interaction of vibration from other equipment such as electric motors, gears, belts, hydraulics, structural resonances and so on, as well as from the movement of the rolling stock itself. Accordingly, a data analytics module will receive the vibration frequency spectrum data and separate out different sources using techniques such as independent components analysis and neural networks, and for each source check if it is functioning normally.

Correct and robust mounting of the BSDU 57 to ensure that the correct area is imaged by the various sensors and that the movements and vibration of the bogie in use do not lead to this area moving out of view or focus. A laser head 14, incorporating a laser of category 3 R or lower, is provided in the BSDU 57 to assist with correct positioning. When switched on, the laser head 14 projects a visible laser spot on a surface showing the position of the imaged area. The overall mounting of BSDU 57 may also require an additional laser range and angle measurement tool to ensure that each device is installed to the same level.

The data from the thermal 10, acoustic 12 and vibration 13 sensors is transferred in real-time to a processor 15, which may take the form of a printed circuit board, a field-programmable gate array (FPGA) or a central processing unit (CPU). The processor 15 applies a series of computer analytics software to individual data streams for determining if an alarm condition exists. The software is modular.

Thermal imaging software modules assess the temperature profile for each row and column of the thermopile array 10, and for each compute the min, max, mean and standard deviation. A desired threshold can be applied to any of these readings to detect an alarm. If an alarm is generated for a measurement at time t, the system first confirms over the next few measurements at times t+i, where i>1 and user set, that the alarm is still active before concluding that there is a genuine fault. This reduces the transmission of false positive alarms.

In the case of acoustic and vibration analysis where a spectrum of data needs detailed analysis, more complex software modules are used which use historic test data to train advanced artificial intelligence techniques such as Independent Components Analysis and Neural Networks to separate the signals and perform tests to check its normality. Other signal processing techniques can also be used as needed.

In circumstances where the processor 15 of the BSDU 57 is unable to perform detailed vibration or acoustic data analysis, the raw data may be passed on for processing elsewhere. A wireless transmitter 16 and receiver 17 are provided on the BSDU to allow communication with other components. A physical data connection 22 is also provided to offer a direct serial connection in case of problems with wireless communication in certain circumstances.

A memory unit 18 is also provided on each BDSU. The memory unit 18 is of relatively small capacity, and is primarily used for buffering raw data from the sensors 10,12,15 and the processor 15 before transmission, as will be explained in greater detail later.

Each BSDU 57 is, in use, installed permanently to a given rolling stock carriage and assigned the carriage identifier. An RFID tag 19 stores the identity of the BSDU 57 to simplify identification during inspection or maintenance.

The BSDU 57 also has a built-in accelerometer and gyroscopic sensor 20 which allows it to sense when the vehicle is in motion. This allows the BSDU 57 to start making measurements automatically when a vehicle starts moving and cease when the vehicle comes to a halt, without an external trigger. The BSDU 57 is therefore active at all times when the vehicle is in motion, and remains dormant when the vehicle is stationary, or after a certain period without movement.

A motion charged battery 21 is provided to power the BSDU 57 so that it can be independent of external power. Motion charged batteries typically do not need to be replaced for several years, whereas other forms of batteries would need to be replaced at least once a year when the rolling stock comes in for maintenance. A power connection 23 is nonetheless also provided to allow charging of the battery from an external source if, for example, the rolling stock has been stationary for a prolonged period, or to allow direct external power connection to the BSDU 57.

Battery powered operation is possible because the entire BSDU 57 is designed to minimise power consumption. As noted above, sampling only takes place when the vehicle is in motion, as identified by the accelerometer and gyroscopic sensor 20. The measurement sampling frequency of the BSDU 57 can also be pre-set at a level sufficient to detect potential problems, but not excessive so as to minimise battery drain. To keep the usual sampling rate as low as possible, and thus keep battery drain low, the rate may also be set to automatically increase from a low base rate only once a potential issue is detected. The BSDU 57 can also be programmed to be in either "shipping mode" where accelerometer/gyro measurements are ignored and therefore no sensing takes place versus "commissioned" mode when it is in service.

The BSDU therefore has built-in intelligence to minimise the amount of data transmission and receipt, adjusting frequency of transmission as needed, and sleep patterns to accommodate periods when the rolling stock is stationary. The sleep patterns mostly apply to data transmission as the unit is in the listening mode at all times (ie the receiver does not go to sleep).

Finally, the BSDU 57 provides a LED indicator light panel 24 on its external body to show alarms or alerts. The panel lights 24 can be programmed to show different condition as "red (alarm)", "amber (risk of alarm)" and "green (good condition)", and can be programmed to show alarms either permanently (eg for a failed component) or only on demand. Avoiding having all alerts illuminate the panel at all times helps to reduce power consumption.

The BSDU 57 will not typically store data under normal conditions. Instead, the software built within BSDU 57 has an alarm trigger which sets off the data recording in the alarm state, so that the BSDU records data from the sensors (eg thermopile pixel matrix statistics, vibration and acoustic signal amplitudes at varying frequencies) only once the measurements are above a fixed threshold.

The BSDU 57 monitors the surface area it is directed to, and has local memory 18 to store some of this data when it becomes useful. The number of BSDUs 57 used per bogie depends on how many components or surface areas need to be inspected. If, for example, a bearing is to be monitored for both sides of the wheel 2, then a bogie will need four BSDUs 57 for monitoring the bearings alone. Extra BSDUs 57 may be provided to monitor brakes 3, axle 7, gearbox 5, motor 9 etc.

Figure 3:
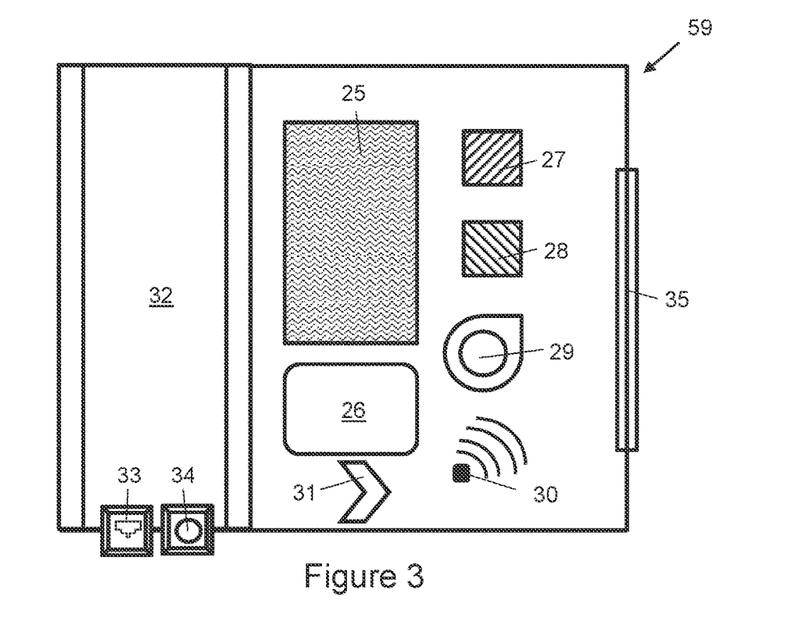
FIG. 3 shows a schematic view of a central unit (CU) according to the present invention.

The second modular device of the invention, called a "Central Unit" (or CU) 59, is schematically shown in FIG. 3. The CU 59 has similar components to the BSDU 57 described above, with the exception of measurement sensors 10,12,13.

One key function of the CU 59 is to receive and relay signals from a group of paired BSDUs 57 using its transmitter 27 and receiver 28. Typical freight rolling stock, in particular, can have an overall length of a kilometer or more, and the BSDUs 57 do not have the data transmission range to send its alarms or alerts over such large distances, partly because of the desire for low power consumption. In use, a number of CUs 59 will be arranged along the length of a train to rely data along the length of the train. Accordingly, the range of the individual transmitters 27 and receivers 28 can again be relatively small, in order to minimise power drain for the CU 59. A GPRS unit 29 is also provided to provide longer range data transmission in the event of a failure at some point in the chain of CUs 59.

The CU 59 also has a processor 25 which allows it to perform limited data analysis required for network maintenance, and a solid state memory unit 26 for storage and buffering data from BSDUs 57, which have lower memory capacity. If the network is under load, for example during an alarm state, then the BSDUs 57 can continue to pile up data at a CU 59 before onward transmission.

As with the BSDU 57 already described, each CU 59 comprises an RFID tag 30 for identification and an accelerometer/gyroscopic unit 31 to trigger their operation, although their operation is slightly different. The CU 59 is always 'on' for data receipt and is constantly in the listening mode. In case where the CU 59 has too much data to transmit, it can override messages from the accelerometer and gyroscopic unit 31 to stop transmitting when train is stationary until any backlog of data transmission is cleared.

A motion charged battery 32 is again provided, along with an external power connection 34 and a serial connector 33 to allow the transfer of data, including diagnostics, to and/or from the CU 59 in case the CU 59 is not capable of sending this wirelessly. Diagnostics, including data about performance, battery levels and charging faults, communication faults, failed internal sensors and so on, can relate not only to the CU 59 itself, but also to its paired BSDUs 57. An LCD display 35 provides a display for such information. The information appears automatically on a rolling screen when faults occur.

Figure 4:
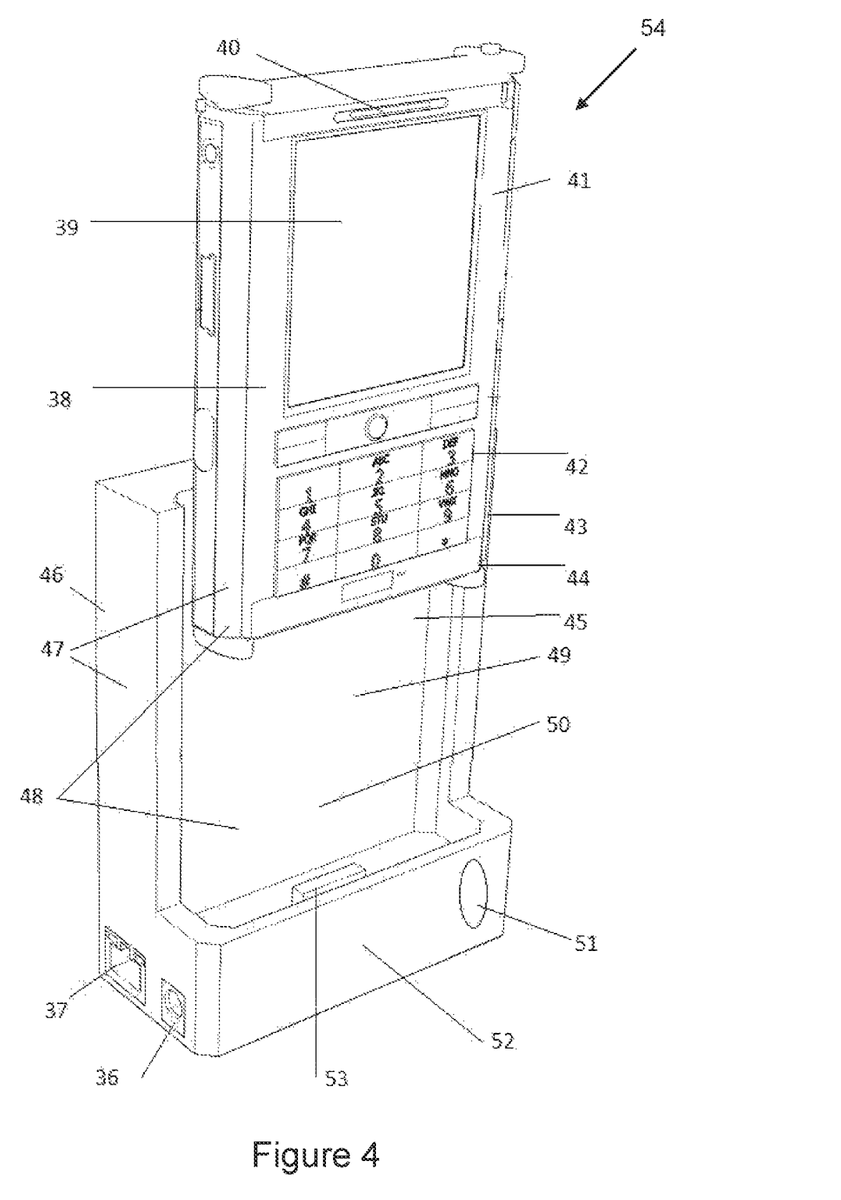
FIG. 4 shows a driver's cabin unit (DCU) according to the present invention.

FIG. 4 shows an example of the third modular device of the invention, the "Driver's Cabin Unit" (DCU) 54 which is an interface device positioned in the driver's cabin. In the most general terms, the DCU 54 comprises a base unit 52 and a removable portable display unit 38.

The base unit 52 is permanently affixed to the console area of the driver's cabin in a locomotive, or another approved location, and is the main 'engine' of the DCU 54 responsible for all forms of data communication and storage. It draws power from the train and acts as a docking station for the portable display unit 38.

The portable display unit 38 comprises a display interface 39, a keypad 42, RFID scanning equipment 43, audio output 40 and a battery 44 to allow handheld operation. The battery 44 of the portable display unit 38 can be charged trough connection with the base unit 52 via a power connector 53 on the base unit 52. The base unit 52 receives mains power through an input connector 36.

Each of the portable display unit 38 and the base unit 52 also comprises a wireless transmitter 47 and receiver 48 for data transfer. The base unit 52 additionally comprises a data connector 37 to allow a physical connection to an external network assisted storage or computer device for removing data or programming the DCU 54.

The display 39 of the portable unit 38 is a touch panel allowing a user to control various commands and review data directly on the screen 39. The display can be used both when the portable display unit 38 is docked on the base unit 52 and when it is disengaged and taken outside of the driver's cabin. The separate keypad 42 can also be used to enter information. For example, the operator may on inspection find that the alarm was false positive and may wish to cancel the alarm with his text input to describe his actions.

The portable unit 38 can beneficially be used for system installation and diagnostic purposes. A maintenance operator can use portable unit 38 of the DCU 54 as a diagnostic tool for fixing problems with CUs 59 and BSDUs 57 at different locations on the rolling stock, during installation and/or maintenance phases, thus avoiding the need for a separate personal computer or similar device.

The RFID scanner 43 can be used to identify specific CUs 59 and/or BSDUs 57 using unique identifiers provided on their RFID tags 19,30. The wireless connection can then be used to obtain detailed diagnostics data and/or drop software updates onto the devices as needed for resetting or changing settings. A local memory 41 allows the storage of settings and configuration files which may be used to update appropriate devices.

With its own built-in transmitter 47 and receiver 48, the portable unit 38 can continue to communicate with the base unit 52 when disengaged during any inspection or other use of the portable unit 38 outside the driver's cabin. It is also able to continue transmitting and receiving data from all CUs 59 in proximity and, through them, data from BSDUs 57. Any changes made by the portable unit 38 are therefore communicated to the base unit 52, which must be synchronised at all times to ensure that the base unit 52 has the latest and current information about the status of the overall system. When the portable unit 38 is docked on the base unit 52, the transmitters and receivers 47,48 are not used, and all communication from CUs 59 takes place directly with the base unit 52.

The base unit 52 of the DCU 54 powers itself on as soon as power becomes available and will shut itself down when no power is available. When the DCU 54 is powered, it is always in an "ON" condition for receiving data, ie it is constantly listening using its receiver 48. If the train stops and there is no buffer for data transmission, its transmitter 47 may go to sleep. An accelerometer/gyroscopic unit 46 is provided to detect movement of the vehicle, and 'wake' or 'sleep' the transmitter 47 as appropriate.

When the train moves, the receiver 48 of the base unit 52 receives data from all nearby train-borne CUs 59, which includes relayed messages from the network of BSDUs 57 and other CUs 59 further along the train. The data includes:

(a) 'heartbeats' showing that the various devices are switched on and working;
(b) alarms if bogie components have failed;
(c) raw data related to alarms in (b);
(d) alarms showing if any devices have low battery levels, communication issues, etc;
(e) signal strength data from CUs 59;
(f) accelerometer data from CUs 59; and
(g) For each CU 59, data relating to which BSDUs 57 are paired with it and their physical location on the train.

The data in (e), (f), and (g) allows a processor 45 within base unit 52 to compute a map of the position of each BSDU 57 and CU 59 on the rolling stock. This provides a visual map of the train showing a layout of the carriages along with the positions of various devices and their current status, for example by colour coding red, amber, green. If any particular device were to show an alarm, the driver can immediately identify exactly where the failure has occurred (eg second bogie, ten carriages behind, left side wheel set). This information is displayed on the screen 39 or the portable unit, and is particularly useful in locating the location of a fault. Once at the appropriate location, the RFID scanner 43 can be used to confirm the identity of a particular BSDU 57 using its RFID tag 19.

All data related to alarms (b) and raw data related to alarms (c) is stored directly in memory 49 which is a solid state disk provided in the base unit. The data is stored in a tabular database which allows its easy retrieval and manipulation. A processor 45 within the base unit 52 allows for further processing of the data before display if required. Any critical alarms are displayed on the main screen 39, showing the position of the relevant device on the visual rolling stock map, and highlighted using the LED indicator 51 on base unit 52. An audio alarm is also provided through the speaker 40.

The memory 18 of the BSDU 57 is limited, and the low power design makes it incapable of sending the data large distances or performing complex analytics that may be necessary for identifying when the measurements represent an alarm condition. Accordingly, each BDSU 57 uses a set protocol to transmit data to a CU 59, which has a larger storage capacity and processing power to make sense of the data. A BSDU 57 is therefore essentially responsible for making measurements, determining if any of them are relevant or indicative of a failure using a fairly basic filter, and then passing on and relevant measurements to a CU 59 for further analysis, storage and/or onward transmission.

The CU 59 collects data of interest from all connected BSDUs, and performs further data analytics as necessary to determine if an alarm condition exists or not. For each BSDU communication, it keeps a record of its identity and receives data in a standard template. It knows which BSDUs 57 are assigned, or paired, to it, and only listens for signals from these paired BSDUs 57. The CU 59 also stores data of interest for historic runs such that a statistical analysis of component behaviour can be performed. Such data can be analysed either by CU 59 itself or passed on to the DCU 54 or an external device for analysis for reporting interesting patterns of component behaviour. For example, correlation between thermal 10, acoustic 12 and vibration 13 sensors may be performed. Finally, CU 59 is responsible for transmitting an alarm, when detected, to the DCU 54.

The DCU 54 is placed next to the train operator. It acts as a display device, providing visual and audio cues when an alarm is detected so that the operator can immediately stop the train when an alert is detected in order to avoid further deterioration of the rail wheel and a potential derailment. The operator is provided with a map display to allow them to see the position of the bogie and failed component with reference to the train layout. The DCU 54 also serves as a tool for managing BSDUs 57 and CUs 59. The DCU 54 keeps a register of their settings, identities, details of their properties such as date of installation, last maintenance date, etc. It is also the point of entry for remote diagnostics and allows for a remote computer to diagnose and repair any problems associated with CUs 59 and BDSUs 57.

The base unit 52 of the DCU 54 is also responsible for direct communication with a remote Operational Control Centre, or OCC 63, as will be explained more fully with reference to FIG. 5. A GPRS link is established through a chip 50 to transmit critical component failures in real-time and data related to these in near-real-time. It is also possible to transmit the position of all carriages attached to the locomotive to the command centre in real-time.

Figure 5:
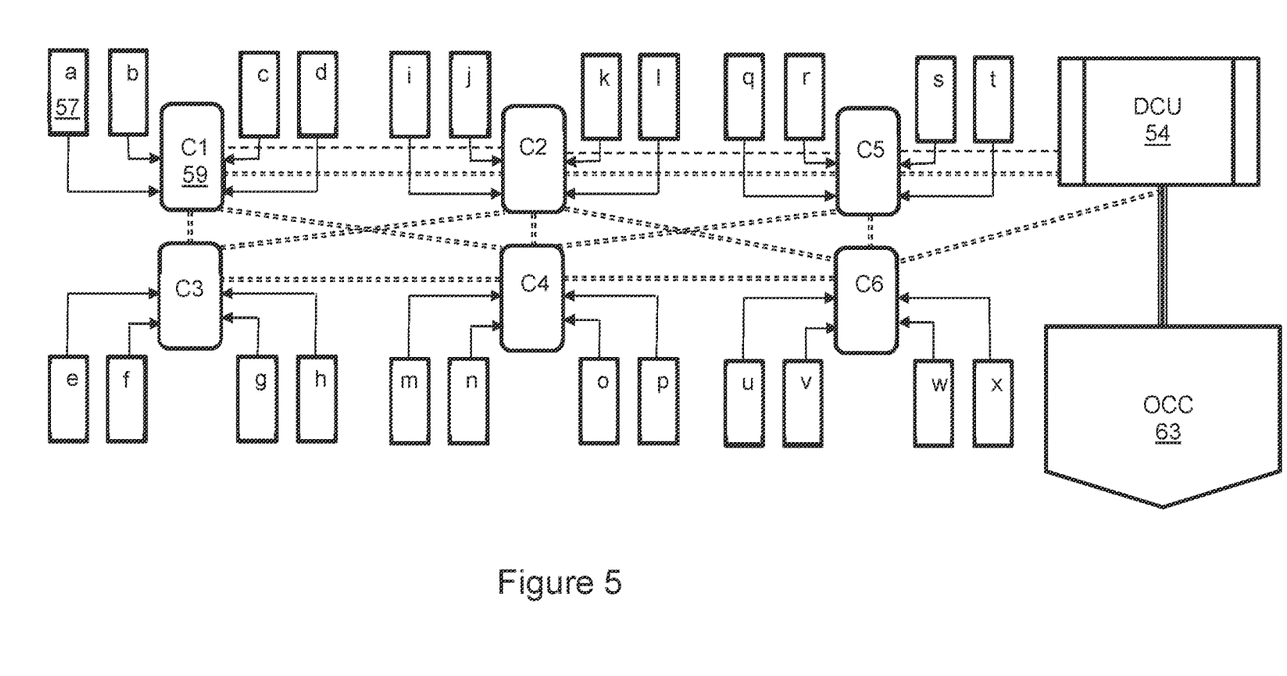
FIG. 5 shows communication paths between the BSDU, CU and DCU and an operational command centre (OCC)

FIG. 5 illustrates the data transmission of the invention, which takes the form of a mesh topology. The overall approach is completely independent of the communication protocols used on a given rolling stock and, in this example, uses a 900 MHz frequency for transmission that differs significantly from the usual Wi-Fi implementations on trains that operate at 2.4 GHz.

FIG. 5 shows a number of BSDUs 57, labelled a to x, each of which is paired to, or connected to, one of a number of CUs 59, labelled C1 to C6. As illustrated, the BSDUs 57 labelled a, b, c and d are connected with a first CU 59 labelled C1, the BSDUs 57 labelled e, f, g and h are connected with a second CU 59 labelled C2 etc. As such, each BSDU 57 is uniquely assigned to a single CU 59.

Each CU 59 provides an intermediate node of data communication between a BSDU 57 and the DCU 54, with a chain of CUs 59 providing relaying information from each BSDU 57 to the DCU 54. Depending on the range of the transmitters built within the BSDUs 57 and CUs 59, typically two CUs 59 per carriage/car will be provided.

The various BSDUs 57 do not try and communicate directly with the DCU 54 or with the OCC 63, instead routing all messages through the assigned CU 59. However, should an assigned CU 59, for example C1, malfunction, its orphaned BSDUs a, b, c and d can be dynamically assigned or paired to another CU 59 in proximity, for example C2, in order to maintain the integrity of the communication network. Orphaned BSDUs 57 can be detected when a CU 59 is not showing the correct number of BSDUs 57.

Each BSDU 57 can transmit a number of different types of alarms and data packets using wireless data communication technology. The alarms can relate to component condition (such as a failing bearing), its own condition (eg low battery) and/or its ability to communicate (eg where the BSDU 57 is unable to pair with a CU 59 or cannot transmit or receive). These alarms are relatively short and are transmitted, in a predetermined format, as soon as the relevant events occur.

Each BSDU 57 and CU 59 transmits a heartbeat message at a set frequency. The heartbeat messages pass through the network and eventually reach the DCU which records them and keeps a log of active devices. If no heartbeat is received from any particular device for a certain predetermined period, then an alarm is generated showing that the device in question is unresponsive.

Alarms related to possible or likely component failure also trigger the collection of raw data by a BSDU 57. The raw data therefore is only collected and relayed when a given device is in the alarm state and not under normal conditions unless specifically programmed to do so, therefore minimising power drain. Two types of data, the alarm message and the raw data containing all physical measurements associated with the alarm, must then be transmitted. As with the previously discussed alarms, the alarm messages showing bogie component failure are relatively short and are instantaneously transmitted, in real-time, to tell the DCU 54 that an alarm has been detected. However, the raw data transmission is more resource and time consuming and therefore requires careful network load consideration during transmission.

The raw data relating to a component failure is not of great significance for the train driver/operator, who needs only to take prompt action based on an alarm message, but it is of significant value for future statistical analysis. A number of statistical software tools used offline can compare the failure data against component properties to identify the nature and possible cause of the failure. Given that different bogies are manufactured by different companies, identifying the root cause of the failure may allow pre-emptive action to be taken on all bogies of the same type in the fleet. Robustness and completeness of the data transmission is thus far more important than instantaneous transmission. To ensure that the transmission network is not flooded, and that data packets are not lost, all raw data is first recorded/buffered onto the memory unit 18 of a BSDU 57 before being transmitted by transmitter 16 to a nearby CU 59 and then relayed onward to the DCU 54 where it is stored in the DCU memory 49.

The BSDU 57 reduces its transmission frequency when its connected CU 59 acknowledges with a 'handshake' that a message has been received. Because each BSDU 57 will be paired with one particular CU 59 at any given time, a single 'handshake' from the connected CU 59 will be sufficient for the BSDU 57 to know that its message has been received.

The CUs 59 in the mesh network are not paired in a similar way, and data from the CUs 59 is transmitted to all other CUs 59 within range without any knowledge of the location of the DCU 54. Accordingly, a CU 59 will reduce its transmission frequency only once it receives at least two handshakes from surrounding CUs 59, which will then pass the message on. The message is prevented from bouncing back to the same CU 59.

If no acknowledgment of a message is received by a CU 59, for example by the CU 59 labelled C1 or C2 at the end of the chain remote from the DCU 54, it will eventually time out and cease transmission. However, if a CU 59 does not receive an acknowledgement signal for a critical alarm for a sufficient length of time, it can use its GPRS unit 29 to communicate the alarm directly to the DCU 54 and/or OCC 63. The use of GPRS for regular transmission is avoided due to its cost and high power consumption, but safety critical information can still be transmitted to the DCU 54 or OCC 63 even when a link in the chain fails. Each BSDU 57 and CU 59 also keeps a register of all sent and received messages to further ensure a robust network.

When the DCU 54 receives a message, it acknowledges its receipt and this message flows in the reverse direction away from the DCU 54 until it reaches the source device that sent the original message. All CUs 59 in the path between the source device and the DCU 54 can then cease transmission of the original message. The source device, for example a BSDU 57 that raised an alarm or a CU 59 that communicated its own alarm status, can also stop transmitting that message with immediate effect.

However, alarm messages relating to component failure are not completely terminated, because the DCU 54 may need continued periodic data to monitor a situation for further deterioration. In these cases, the BSDU 57 continues to transmit alarm messages and related data until the problem is corrected, although the transmission frequency of alarm messages may be reduced by the BSDU 57 once the DCU 54 sends a confirmation message to the BSDU receiver 17 that the original alarm message has been received. For example, if the DCU 54 acknowledges an alarm sent from the BSDU 57 labelled p, then the CUs 54 labelled C6, C5, C4 and C2 will stop sending the original message to DCU 54 as soon as they receive the acknowledgement message from DCU 54. The BSDU 57 labelled p then reduces its sampling/transmission frequency, but continues sending data at fixed intervals. The DCU 54 can then continue to monitor the alarm condition over time, while the lower sampling rate avoids flooding the communication network with messages.

Although the capacity of the memory unit 49 on the DCU 54 is far greater than that of an individual BSDU 57 or CU 59, it is still desirable for the DCU 54 to be able to transmit data to a remote location such as the OCC 63. A single DCU 54 will be permanently equipped to a locomotive, but the cars/carriages connected to the locomotive will change over time. Therefore, at any given time the data contained within the DCU 54 may relate to carriages which are no longer attached to the locomotive. The OCC 63 is a physical back office facility containing the necessary IT infrastructure to house data from a large variety of BDSUs 57 and CUs 59. It provides the main storage for all data for all alarms (message and raw data) and condition data gathered over time, and because the data from each BSDU 57 is provided with a unique identifier attached, it allows compilation of all historical data from a particular BSDU 57, and therefore relating to a particular component, even if transmitted by a number of different DCUs 54 over the component's lifetime.

Figure 6:
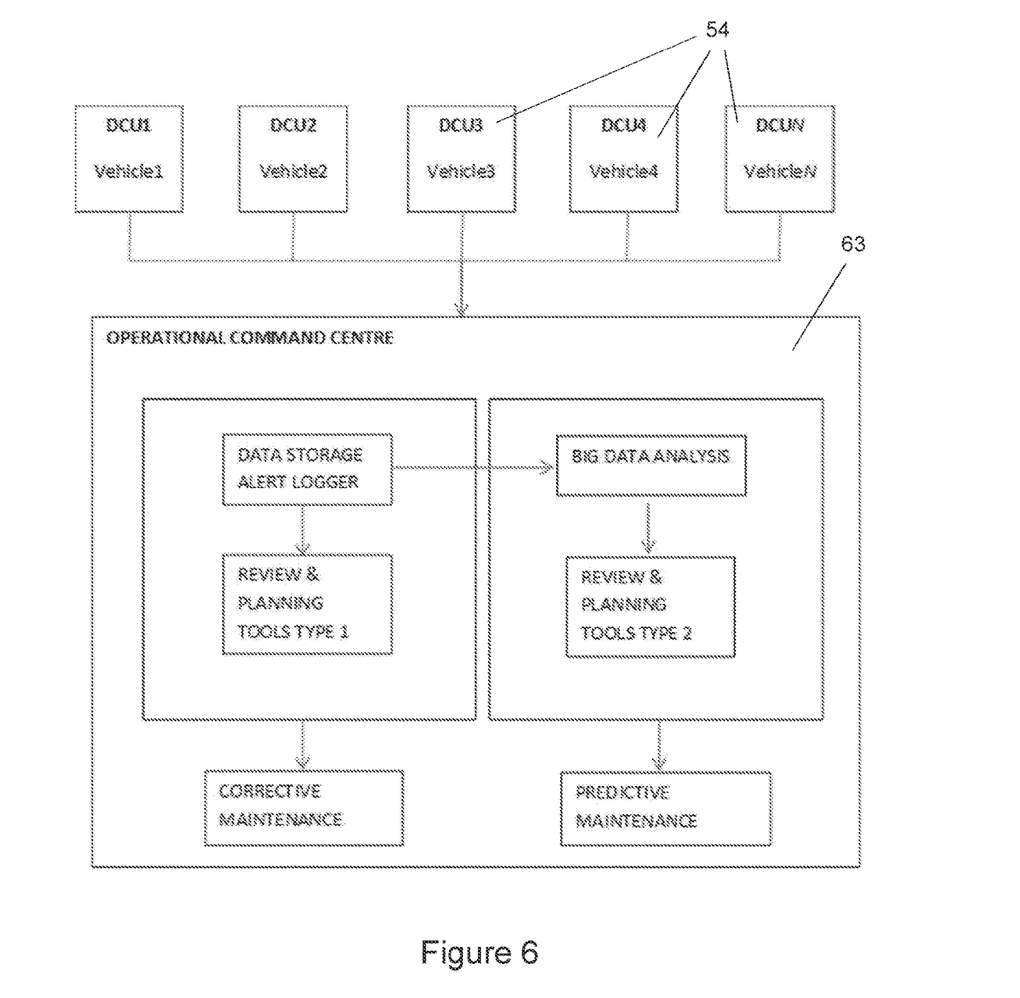
FIG. 6 is a diagram illustrating data flow from multiple vehicles and its analysis in the OCC for corrective and predictive maintenance.

FIG. 6 shows how the data flows from a number of DCUs 54, each associated with different train, to an OCC 63. It should, however, be understood that the indicated data communication could instead come from one or more CUs 59, for example where a DCU 54 is not present or not available, or simply if review of the data on a console of a DCU 54 is not required.

The data flow for corrective and predictive maintenance are shown separately. With trackside systems in existence today, predictive maintenance of vehicle borne components is not possible. The data transmission to OCC 63 will be wireless and could use either a cellular router or Wi-Fi hotspots. The system may be configured to only provide alert data which includes sensor measurements during a period when the measurements are outside of set thresholds that represent normal expected values. Once the system goes above the threshold, all measurements made at a set frequency are transmitted for the sensor indicating an alarm condition. The settings for variables including sensor measurement thresholds, frequency of sensor sampling and frequency of data transmission in alarm condition are remotely configurable.

Multiple thresholds may be set. For example, if the heat measurement on a particular component surface is greater than 30° C. above ambient, then this may indicate a lower category alarm which triggers the associated BDSU 57 to start transmitting all temperature readings for that component to the CU 59 and/or DCU 54, which is to be stored and passed on to the OCC 63. If the temperature becomes greater than 60° C. above ambient, the system now goes into a critical state, and alerts the OCC 63 and, if present, the DCU 54 to take action. Temperature readings continue to be recorded, stored and transmitted. The frequency of transmission may now by higher given that the system is in a higher state of alert.

The alarm state data generated by the BDSU 57 will arrive into the OCC 63. It is archived and tagged based on the identity of the vehicle the sensor it is mounted on (eg railcar identification number), substructure it is mounted on (for railways this may be the bogie identification number) and its relative position (eg left or right). Additional data on the time of failure and the geographic location of the vehicle may also be available. In a typical scenario, the OCC 63 will consist of data storage and review tools for corrective maintenance. These tools will assist the OCC 63 to identify that a failure has occurred, and allow the user to take action such as stop the vehicle and get a human operator or maintenance team to evaluate vehicle safety. Further automated or manual planning tools may be used to organise maintenance.

As a part of our invention, statistical analytics tools at OCC 63 can use the alarm state data from the BDSUs 57. Such data describes the condition of a component when it enters into an alarm state which could be much before the component enters into a critical failure state or even fails. Over a period of time, significant volumes of data on component condition can be collected. It is important to note that such historical data on component condition is not available with trackside monitoring equipment in use today and therefore it is impossible at present to perform predictive maintenance. Such historical data can be used for predictive maintenance. It can be charted and evaluated with statistical tools to differentiate between different types of problems, estimate time to failure and determine the root cause of the problems (manufacturing issues versus wear and tear). Our solution provides for tools that can perform data classification, clustering, forecasting and planning on such data. Classification tools may be used to classify component condition and determine severity of the problem. Multi-sensor data may be integrated for accurate decision making and novelty detector tools may be used to determine abnormal behaviour. Clustering tools may be used to cluster the data from multiple vehicles and sensors to determine similarities between feature values and to determine commonalities. For example, the clustering analysis may indicate that the same problem occurs with components that have similar loads, or similar other characteristics. Forecasting tools such as regression analysis may be used to determine performance decay over time, and time to failure for components. Such analysis can be multivariate taking into account various component and non-component features of operation. Finally, maintenance planning tools for corrective and predictive maintenance may be used by the end-user to manage the repair and replacement of components.

The system can therefore provide a set of computational and statistical data for evaluating alarm state data from the first modular device for determining component condition, root cause of condition deterioration, and time to failure.

The storage capacity of the memory unit 49 on the base 52 of the DCU 54 is sufficient that transmission to the OCC 63 may be performed only periodically, rather than in real-time. Alternatively, any alert/alarm messages may be transmitted in real-time to the OCC 63, with the raw data transmission carried out later.

Figure 7:
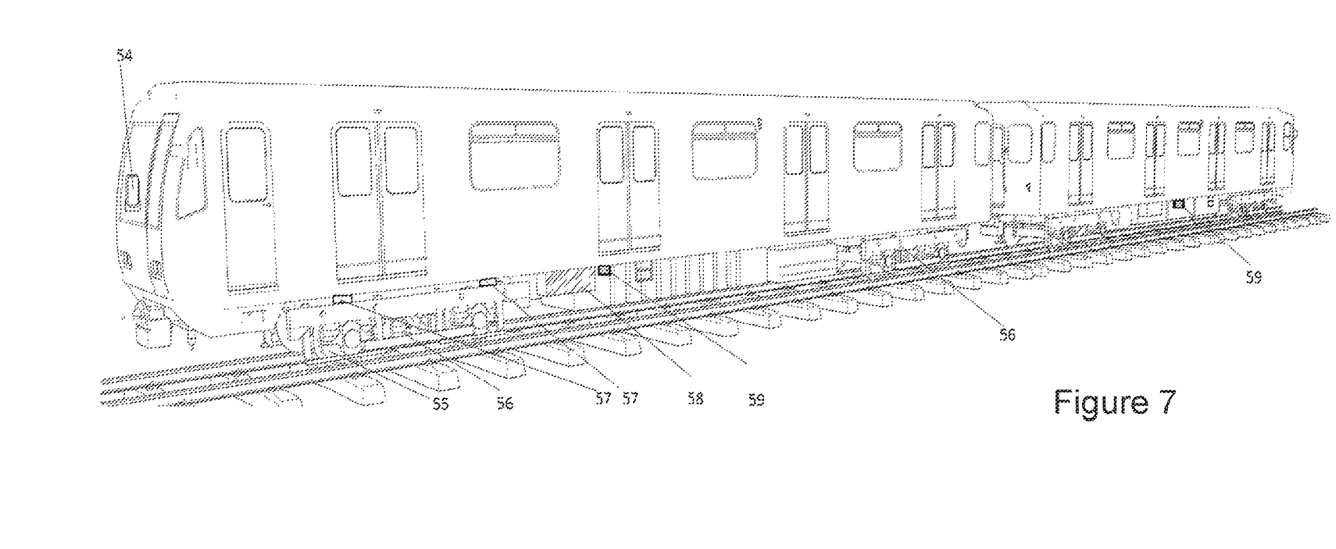
FIG. 7 shows a typical rolling stock configuration showing the position of various components of the invention on a train.

FIG. 7 shows how components of the invention may be mounted on a train. The DCU 54 is shown mounted in the driver's cabin at the front of the train, and the locations of two BSDUs 57 are indicated on the bogie 56 at this end of the train, adjacent the wheels 55. Two more BSDUs 57 would be provided on the opposite side of the train, obscured in FIG. 7, to monitor the wheels on that side. It will also be understood that additional BSDUs 57 could be provided to monitor additional components if required, and that the arrangement would be repeated for the other bogies 56 further along the train to provide a network or mesh similar to that shown in FIG. 5.

A CU 59 is located approximately half way along each carriage shown in FIG. 7, between a pair of bogies 56. Again, a further CU 59 would be provided on the opposite side of the carriage. The wireless transmission of the invention avoids the need for cabling to be provided in or around the train carriages, and is therefore of great benefit during installation. However, the large amount of metal present underneath a train carriage causes difficulty with wireless transmission. Positioning the CUs 59 at the sides of each carriage therefore improves the reliability of the data transfer, which is important in ensuring a robust system.

Motion and location sensors 58 may also be provided as part of the system as indicated. These additional sensors can provide CUs 59 and/or the DCU 54 with real-time information such as vehicle speed, acceleration, tilt, track curvature, and GPS location. Details of where the train was, its speed and acceleration, time travelling from last stop, ambient temperature, track properties, etc can then be appended to the usual alarm data when generated, and transmitted as described above.

The invention includes several features which set it apart from traditional trackside monitoring of components.

By mounting monitoring devices on or close to the bogie on a train, the devices are located close to, and in a static relationship with, components to scan. This ensures a clear consistent view of the components in the scanning process. Monitoring the bogie components constantly, rather than at set intervals along the trackside, also generates detailed statistics about component behaviour over time, which can be used for predictive maintenance.

The devices are designed to communicate with each other using low power in a manner that the detection of alarms can be communicated effectively from the sensor side to the driver such that the train can be stopped. The system also provides for communication to a remote operational command centre. The communication protocol allows for the data to be relayed between devices until it reaches its expected destination, independent of the train's own communication system and designed not to interfere with it. The system is also designed for changes to devices in a chain structure and still being able to communicate between sensors and the driver. For example, if a train carriage is replaced with another one, the system will automatically calibrate to recognise the new devices on this newly introduced carriage and use them in message relaying.

The data communication element of the invention is built upon the principles of ensuring data integrity, high quality data transmission with sufficient redundancy with a mesh network to avoid complete transmission failure between alarm source and DCU 54, low power consumption for data transmission, and providing a complete set of data on device status, component failure and data load.

Data integrity is assured through intelligence embedded within the system that compares transmitted data against expected data. For different forms of data, a well-defined data format is used with certain numbers of bytes allocated to each message transmission. If any data is lost or corrupted, it is not acknowledged by the receiving CU 59 which discovers that not all data has been received and must be sent again. Failsafe measures such as GPRS units 29 allow for the integrity of the transmission system to be preserved even if one transmission device in the chain fails to work. The DCU 54 is also sent a message to say how the data has been routed in such cases, along with details of the position of the failed device in the network.

Low power consumption requires that devices transmit only when necessary, and can change their transmission frequency dynamically depending on network load. Transmitting at very high frequency will overload the system, overwhelm memory and processing, and essentially create a network traffic jam with high levels of power consumed.

Finally, the devices must maintain their own registers to record all messages received and sent, all data buffered for transmission, and should cancel transmitting a message towards the DCU if an acknowledgement of its receipt has been sent by the DCU.

The system is modular to allow the use of multiple sensor devices, each focussed on monitoring a set component. This allows for the technology to be used for inspecting any number of components, not simply wheels or bearings. A combination of thermal, acoustic, and/or vibration sensors can be used. Each one of them has their own strength, and a combination of their analysis can provide a good estimate on the fault. The scanning processing is non-contact so the devices need not touch the component surface.

The entire system is designed for low power consumption and for using motion charged batteries. The power dependence on the vehicle is therefore minimal except for the use of analytics and statistical processing on a device which can easily have mains power in the driver's cabin.

The description and associated drawings are provided only as an example of the invention. It should be understood that certain modifications would be possible without departing from the scope of the invention as claimed.

For example, motion charged batteries could be replaced with alkaline or lithium batteries and the thermopile array could be replaced with an array of a different size or with a different non-contact thermal sensor.

The 900 MHz transmission frequency mentioned for the specific example was chosen to ensure no conflict with the 2.4 GHz transmissions typically used for Wi-Fi implementations etc, but it should be clear that other frequencies would also be suitable.

The method and apparatus can also be used for other parts of rolling stock monitoring than those described where component failure shows changes in heat, acoustics and vibration. Similar inspection of underlying infrastructure, such as rails or other parts of the track, would also be possible as the train passes over or by. A GPS receiver or similar location sensor would provide the location of a potential failure in such circumstances.

In all cases the system will help to prevent accidents by alerting the train driver or a command centre in real-time of failed components, and assist with timely maintenance of components that have failed or are close to failure. The invention may also find application in other vehicles where similar installation and data transmission problems apply.

What is claimed is:

1. A vehicle mountable modular monitoring system for monitoring one or more components of a bogie or railroad truck, the system comprising:
    first and second modular devices mountable to the vehicle, the first modular device being configured for mounting adjacent a component to be monitored and comprising:
        a power source,
        one or more sensors including a non-contact temperature sensor for monitoring a temperature of said component, and
        a first wireless transmitter for transmitting data wirelessly from the first modular device to the second modular device;
    the second modular device comprising a wireless receiver for receiving data transmitted by the first modular device.

2. The vehicle mountable modular monitoring system of claim 1, wherein the non-contact temperature sensor is a thermal imaging sensor for generating thermal images of the component.

3. The vehicle mountable modular monitoring system of claim 1, wherein the power source comprises a battery.

4. The vehicle mountable modular monitoring system of claim 1, wherein the first modular device generates alerts based on a comparison of sensor readings from the one or more sensors with one or more threshold values and wherein the data transmitted from the first modular device includes said alerts and the associated raw sensor readings.

5. The vehicle mountable modular monitoring system of claim 1, further comprising a third modular device comprising a wireless receiver and wherein the second modular device comprises a wireless transmitter to relay the data received from a first modular device to the third modular device.

6. The vehicle mountable modular monitoring system of claim 5, wherein the third modular device provides one or more of visual and audio output to a user based on the data received by the third modular device.

7. The vehicle mountable modular monitoring system of claim 5, wherein the third modular device comprises a memory unit to store received data to enable further data analytics.

8. The vehicle mountable modular monitoring system of claim 5, wherein a plurality of second modular devices are provided to form a chain and relay data beyond the transmission range of the wireless transmitter of each second modular device.

9. The vehicle mountable modular monitoring system of claim 5, wherein the data transmitted from the first modular device includes location data of the mounting position of the first modular device.

10. The vehicle mountable modular monitoring system of claim 5, wherein a sampling rate of the one or more sensors is variable during use.

11. The vehicle mountable modular monitoring system of claim 5, wherein the transmission rate of one or more of the first and second modular devices is variable during use.

12. The vehicle mountable modular monitoring system of claim 5, wherein the first modular device comprises one or more of an accelerometer and a gyroscopic sensor to detect movement of a vehicle and deactivate the one or more sensors or the transmitter when no movement is detected.

13. The vehicle mountable modular monitoring system of claim 5, wherein the first modular device comprises a laser aligned with the field of the one or more sensors for aligning the one or more sensors with a component to be monitored when mounting the first modular device.

14. The vehicle mountable modular monitoring system of claim 5, wherein the third modular device comprises a base unit and a portable unit that can be disengaged from the base unit.

15. The vehicle mountable modular monitoring system of claim 14, wherein the portable unit comprises an RFID scanner and the first modular device comprises an RFID tag for identification.

16. The vehicle mountable modular monitoring system of claim 5, wherein the first modular device comprises a plurality of sensor types working in combination.

17. The vehicle mountable modular monitoring system of claim 16, wherein the recognition of a defective component and/or the generation an associated alarm is based on analysis of the information provided collectively by said plurality of sensor types.

18. A method of monitoring a vehicle component over time with the vehicle mountable modular monitoring system of claim 1, comprising:

taking periodic sensor readings relating to at least one of the temperature, vibration and noise emitted by the component during use;

relaying data from said sensor readings to a location remote from the component; and analysing said data to identify faults or predict failure of said component.

* * * * *